United States Patent [19]

Hall et al.

[11] 4,175,569

[45] Nov. 27, 1979

[54] SUBSTITUTED-1-OCETYL-3,3-DIMETHYL-CYCLOHEXANE EMPLOYED IN FLAVORING TOBACCO COMPOSITIONS

[75] Inventors: John B. Hall, Rumson; Mark A. Sprecker, Sea Bright; Frederick L. Schmitt, Holmdel; Manfred H. Vock, Locust, all of N.J.

[73] Assignee: International Flavors & Fragrances Inc., New York, N.Y.

[21] Appl. No.: 834,501

[22] Filed: Sep. 19, 1977

Related U.S. Application Data

[60] Division of Ser. No. 753,617, Dec. 22, 1976, Pat. No. 4,081,429, which is a continuation-in-part of Ser. No. 713,429, Aug. 11, 1976, Pat. No. 4,021,480.

[51] Int. Cl.$^2$ .................. A24B 3/12; A24D 1/00; A24D 1/18
[52] U.S. Cl. .................. 131/9; 131/2; 131/15 R; 131/17 R; 131/144
[58] Field of Search ........... 131/144, 17 R, 15 R, 131/9; 260/586 R; 252/522, 586; 426/538, 589, 650

[56] References Cited

U.S. PATENT DOCUMENTS

| | | | |
|---|---|---|---|
| 3,875,241 | 4/1975 | Corber et al. | 260/586 R |
| 3,890,370 | 6/1975 | Buchi et al. | 260/586 R |
| 3,927,107 | 12/1975 | Schulte-Elte et al. | 260/586 R |
| 3,929,895 | 12/1975 | Hall | 260/586 R |
| 3,946,078 | 3/1976 | Rautenstramh et al. | 260/586 R |
| 3,948,815 | 4/1976 | Corber et al. | 260/586 R |
| 3,956,392 | 5/1976 | de Haan et al. | 260/586 R |
| 4,021,488 | 5/1977 | Hall et al. | 260/586 R |

*Primary Examiner*—V. Millin
*Attorney, Agent, or Firm*—Arthur L. Liberman; Franklin D. Wolffe

[57] ABSTRACT

Described is a genus of substituted 1-acetyl-3,3-dimethylcyclohexanes having the structure:

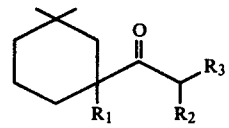

wherein $R_1$ is methyllyl, $R_2$ is hydrogen and $R_3$ is hydrogen, or wherein $R_1$ is hydrogen, $R_2$ is methyllyl and $R_3$ is methyllyl. The above compound is employed in combination with smoking tobacco. a phase transfer agent and in a two phase system according to the reaction:

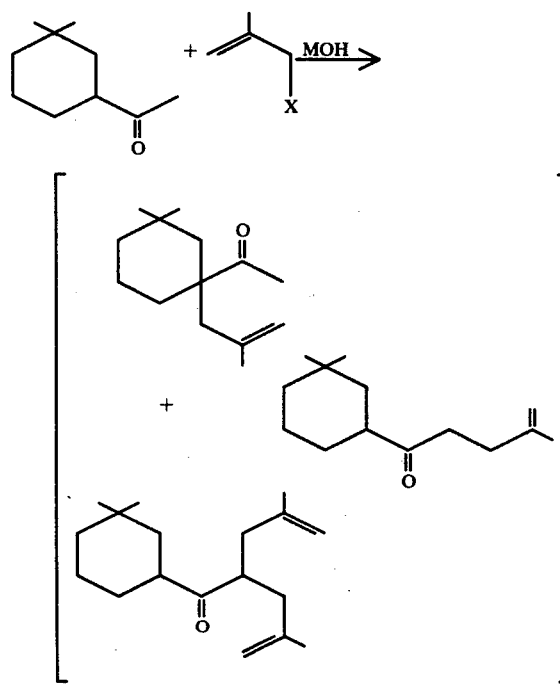

wherein X is chloro or bromo, processes for adding such 1-acetyl-3,3-dimethylcyclohexane derivatives to consumable materials whereby:

(i) In foodstuffs and medicinal products, fatty, sweet, fruity, citrus, green and vegetable-like aromas and fatty, sweet, fruity, citrus, vegetable-like and waxy flavor characteristics are augmented or enhanced;

(ii) In perfumes and perfumed articles, green, herbaceous, melony and fruity aromas with galbanum-like, ginger-like and citrusy nuances are imparted, augmented and/or enhanced; and (iii) In tobaccos and tobacco flavors, green, sweet, fruity, floral and Virginia tobacco-like flavor and aroma nuances are augmented and/or enhanced in the mainstream and in the sidestream on smoking and, in addition, prior to smoking and flavor compositions, perfume compositions and tobacco articles and foodstuffs and perfumed articles containing such 1-acetyl-3,3-dimethylcyclohexane derivatives.

3 Claims, 4 Drawing Figures

IR SPECTRUM FOR EXAMPLE I

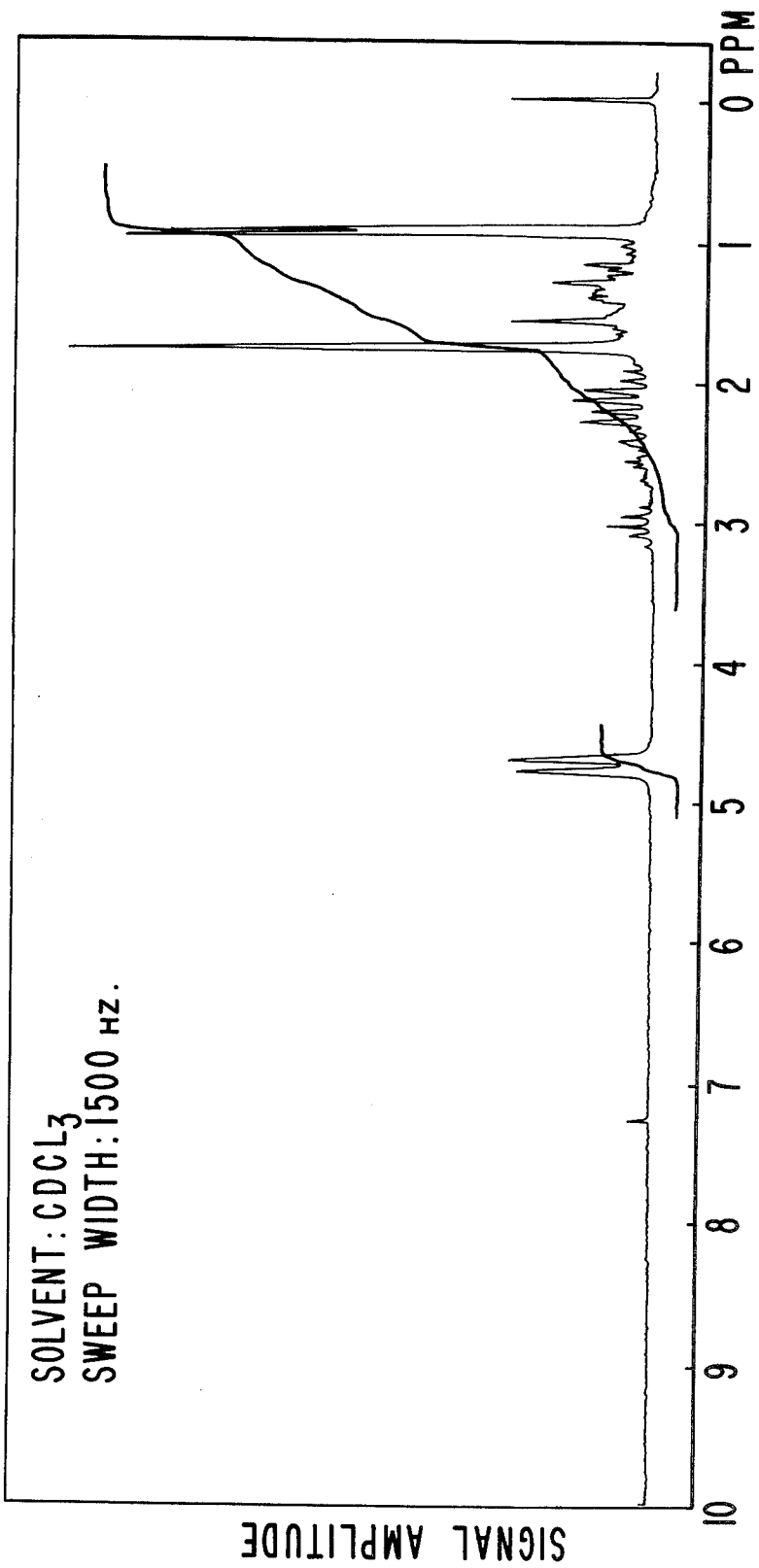

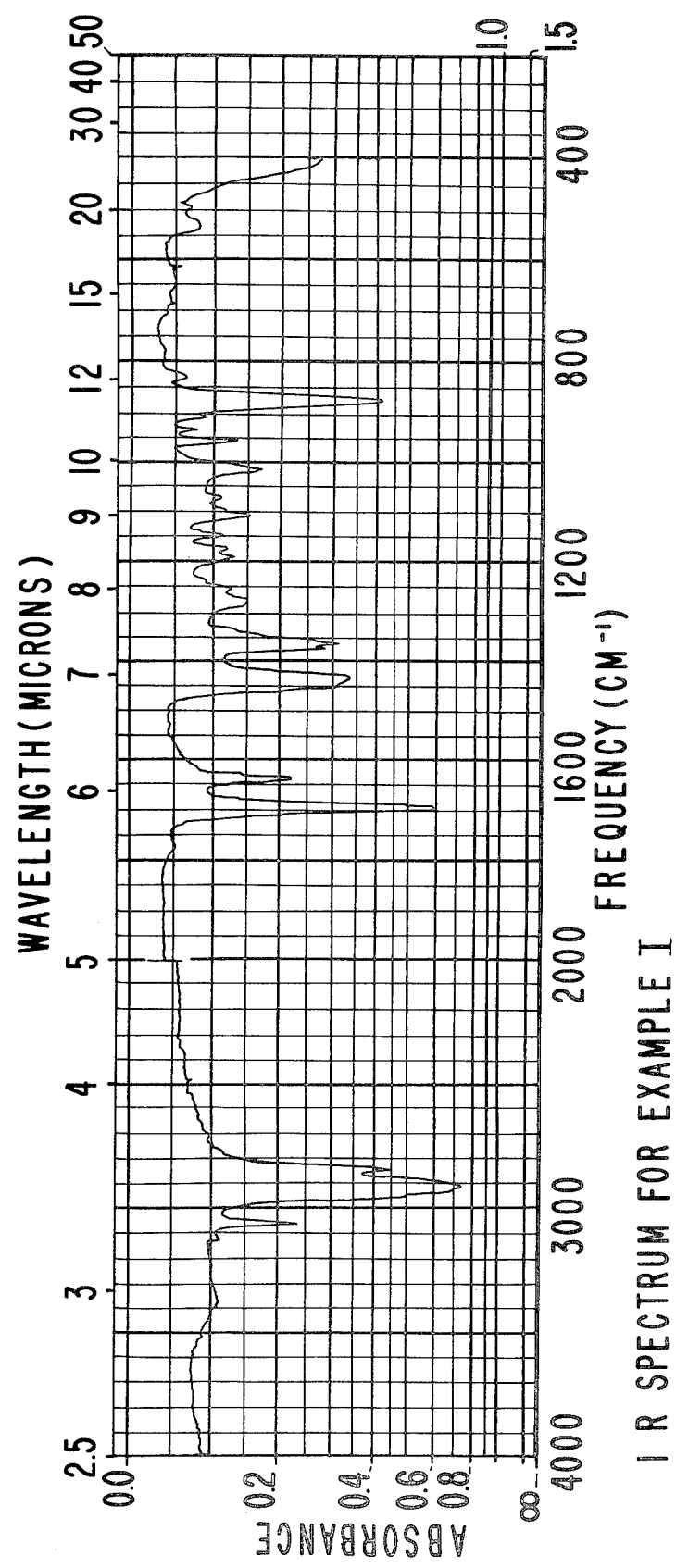

SUBSTITUTED-1-OCETYL-3,3-DIMETHYLCYCLOHEXANE EMPLOYED IN FLAVORING TOBACCO COMPOSITIONS

This is a division of application Ser. No. 753,617 filed Dec. 22, 1976, now U.S. Pat. No. 4,031,479 which in turn, is a continuation-in-part of application Ser. No. 713,429 filed on Aug. 11, 1976 now U.S. Pat. No. 4,021,480.

BACKGROUND OF THE INVENTION

The present invention provides 1-acetyl-3,3-dimethylcyclohexane derivatives having the generic structure:

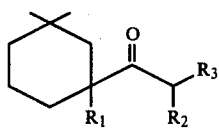

wherein $R_1$ or one or both of $R_2$ and/or $R_3$ is methallyl and the other of $R_1$ or $R_2$ and/or $R_3$ is hydrogen and a straightforward, economical process directed towards synthesizing such 1-acetyl-3,3-dimethylcyclohexane derivatives by reaction of methallyl halides with acetyl-3,3-dimethylcyclohexane, and utilization of such 1-acetyl-3,3-dimethylcyclohexane derivatives for their organoleptic properties in perfumes, perfumed articles, foodstuffs, medicinal products, tobaccos and tobacco articles.

In the perfumery art there is a considerable need for substituents having green, herbaceous, melony and fruity aromas with galbanum-like, ginger-like and citrusy nuances. Specifically described are materials having such a profile but which do not discolor with age. Such fragrance materials have a wide utilization in perfume formulations and perfumed articles. A minimum amount of such materials that give rise to these properties is available from natural sources but the natural materials are subject to wide variations in quality, are expensive, and are limited or often in critically short supply.

Furthermore, there is a continuing search for compositions which can vary, modify, fortify, enhance, augment or otherwise improve the flavor and aroma of foodstuffs, chewing gums and medicinal products. To be satisfactory, such compositions should be stable, non-toxic and blendable with other ingredients to provide its own unique flavor and aroma nuance without detracting from the co-ingredients. Preferably, such compositions should be naturally occurring or present in natural foodstuffs so that their ingestible safety can be readily recognized or, such compositions should be similar to those materials present in natural foodstuffs so that their ingestible safety can be recognized. These materials should be capable of being synthesized in a simple and economical manner. The need for safe flavors in the fruity flavor area, e.g. citrus flavor area, is well-known, particularly in the beverage flavor area and in the yogurt flavor area. More specifically, there is a need for the development of non-toxic materials which can replace natural materials not readily available, having sweet, fruity, citrus, green and vegetable aroma and flavor characteristics.

Firmenich's Dutch published application 7500838 discloses the preparation of the compound having the structure:

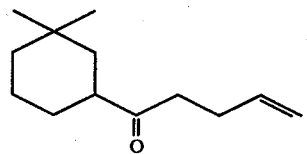

and discloses its use in perfumery and in augmenting foodstuff flavors. The perfumery use of this compound and other members of its class as "floral, green, herbaceous and chypre" useful in galbanum resinoids is also disclosed.

The compounds disclosed in Dutch published application 7500838 have organoleptic properties which causes them to be different in kind from 1-acetyl-3,3-dimethylcyclohexane, which has unobvious, unexpected and advantageous characteristics in the field of augmenting or enhancing the organoleptic impressions of foodstuffs, foodstuff flavors, perfumes, perfumed articles and medicinal products.

Insofar as relevant prior art concerning the process for preparing 1-acetyl-3,3-dimethylcyclohexane is concerned, German Pat. No. 1,244,784, issued on July 20, 1967, discloses the reaction:

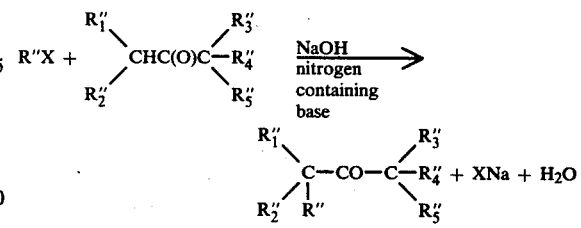

wherein R can be one of alkyl, alkenyl, allyl, propargyl, cyclohexyl or benzyl; X is chloro or bromo, and $R_1$, $R_2$, $R_3$, $R_4$ and $R_5$ can be hydrogen, alkyl, alkenyl or phenyl. The reaction of the German Patent is limited to ketones. However, the nature of the reaction is different in kind from the reaction of the instant invention.

German Pat. No. 1,244,784 corresponds to British Pat. No. 1,059,839 published on Feb. 22, 1967, entitled, "Process for Preparing Ketones and Novel Ketones so Prepared." Tamai, et al, U.S. Pat. No. 3,983,175 issued on Sept. 28, 1976, (a continuation-in-part of Ser. No. 417,201 filed on Nov. 19, 1972, now abandonded) discloses a process for producing a ketone which has a replaceable hydrogen atom on the carbon atom in the alpha position to the carbonyl group in the presence of an aqueous alkali metal hydroxide and a nitrogen-containing base as a catalyst, e.g., primary amines, secondary amines, tertiary amines, and quarternary ammonium salts. The nature of the reaction described in the patent by Tamai et al is different in kind from the reaction of the instant invention. The same holds true for Meuly, et al, U.S. Pat. No. 3,668,255 issued on June 6, 1972, a continuation-in-part of Ser. No. 241,036 filed Nov. 29, 1962, now abandoned.

BRIEF DESCRIPTION OF THE DRAWINGS

FIG. 3 represents the NMR spectrum for the compound 1-(2-methallyl-5-methyl-4-pentenoyl)-3,3-dimethylcyclohexane produced according to Example I.

FIG. 4 represents the Infrared spectrum for the compound 1(b 2-methallyl-5-methyl-4-pentenoyl)-3,3-dimethylcyclohexane produced according to Example I.

THE INVENTION

Figure 1:
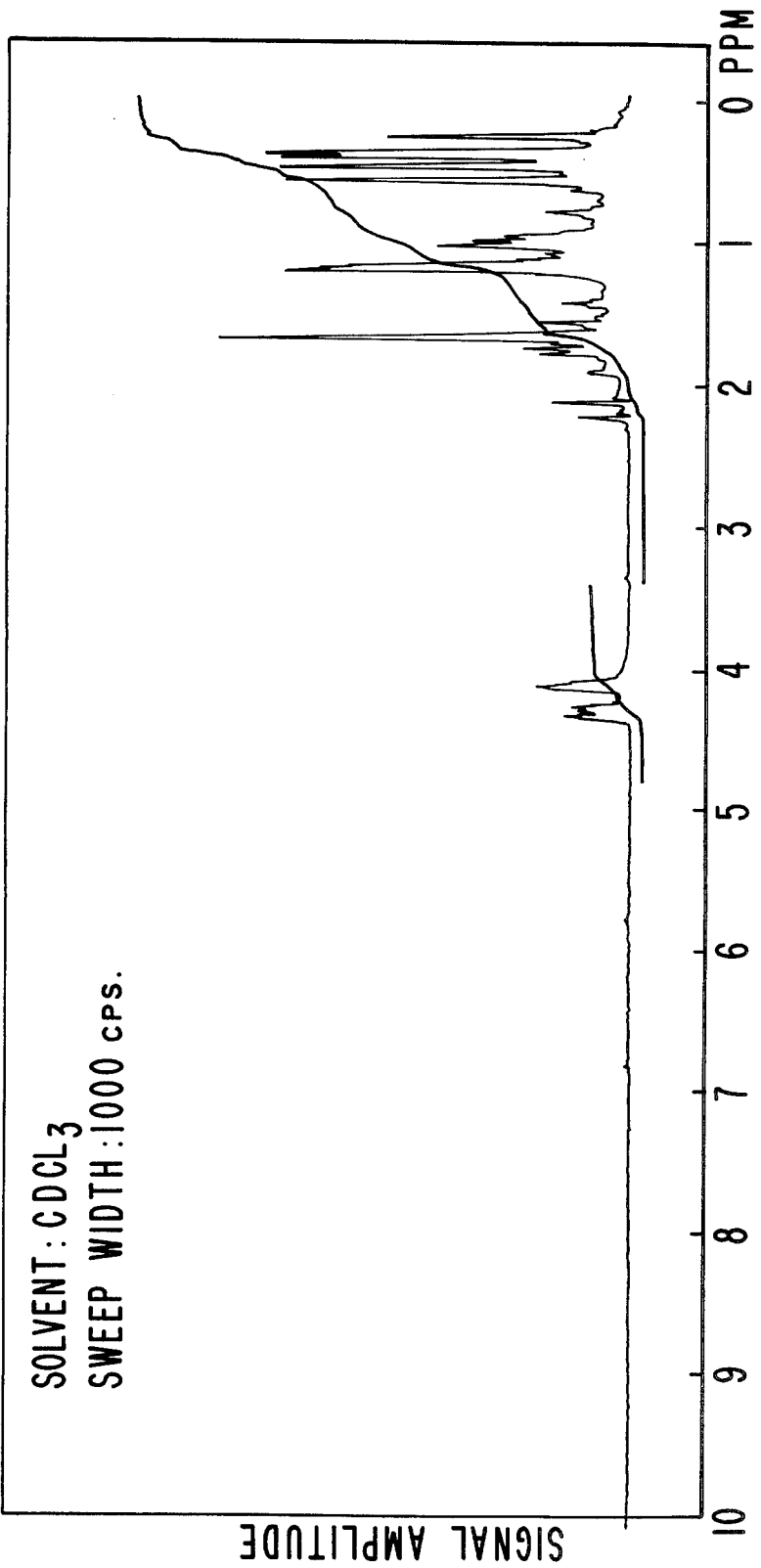
FIG. 1 represents the NMR spectrum for 1-acetyl-1-methallyl-3,3-dimethylcyclohexane produced according to Example I.

The present invention relates to the novel compounds, 1-acetyl-1-methallyl-3,3-dimethylcyclohexane and 1-(2-methallyl-5-methyl-4-pentenoyl)-3,3-dimethylcyclohexane having the generic structure:

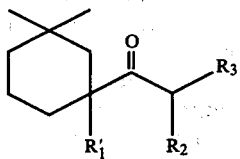

wherein $R_1$ or one or both of $R_2$ and/or $R_3$ is methallyl and the other of $R_1$ or $R_2$ and/or $R_3$ is hydrogen, a process for producing same, and perfumes, perfumed articles, foodstuffs, foodstuff flavorings, medicinal products, tobaccos and tobacco flavorings containing 1-acetyl-3,3-dimethyl-cyclohexane derivatives having the above generic structure.

The compounds having the structure:

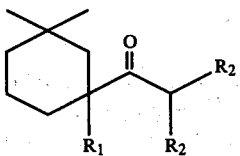

are capable of augmenting or enhancing orange flavors by providing thereto sweet, fruity, citrus, green aromas with sweet, fruity, citrus flavor characteristics.

The compounds having the generic structure:

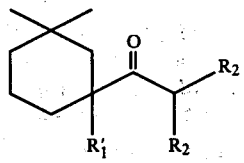

are also capable of modifying or enhancing the aroma characteristics of perfumed compositions and perfumed articles by imparting thereto or augmenting or enhancing green, herbaceous, melony and fruity aromas with galbanum-like, ginger and citrus nuances thus fulfilling a need in the field of perfumery.

The compounds having the generic structure:

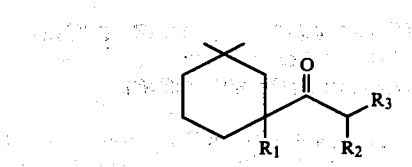

are also capable of modifying, augmenting or enhancing the aroma characteristics of tobacco and tobacco compositions and smoking tobacco articles by imparting, augmenting or enhancing green, sweet, fruity, floral and Virginia tobacco-like aromas prior to and on smoking in the mainstream and in the sidestream.

The compounds having the generic structure:

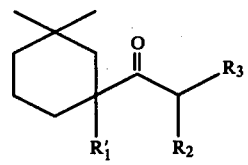

wherein $R_1$ or one or both of $R_2$ and/or $R_3$ is methallyl and the other of $R_1$ or $R_2$ and/or $R_3$ hydrogen, are produced by reacting acetyl-3,3-dimethylcyclohexane with a methallyl halide in the presence of an inert solvent and an alkali metal hydroxide in the presence of a "phase transfer agent." The reaction is carried out in a two phase system. Thus, one aspect of our invention is illustrated in the following reaction:

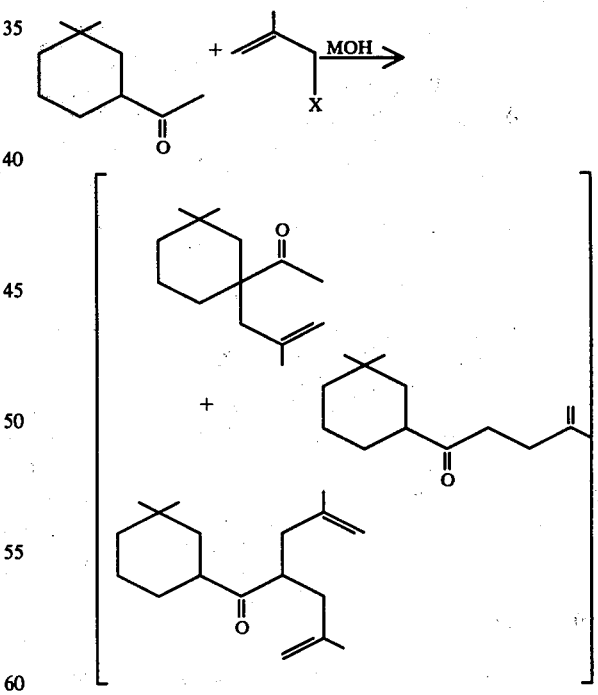

wherein M is alkali metal and X is chloro or bromo.

One aspect of our invention involves the aforementioned process comprising the step of placing the reactants for the process and the base, respectively, in two immiscible phases; an organic phase and either (i) an aqueous base phase or (ii) a solid base phase with the reactants being located substantially entirely in the first mentioned organic phase and the base being located substantially entirely in the second mentioned phase; and adding to this two phase system a "phase transfer agent" which may be one or more of several organic quaternary ammonium salts.

Specific examples of phase transfer agents useful in our invention are as follows:

Tricapryl methyl ammonium chloride;
Cetyl trimethyl ammonium chloride;
Cetyl trimethyl ammonium bromide; and
Benzyl trimethyl ammonium hydroxide. In general, the phase transfer agents most preferred have the generic formula:

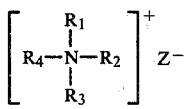

wherein at least one of $R_1$, $R_2$, $R_3$ and $R_4$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and $Z^+$ is an anion such as chloride, bromide and hydroxide.

The process of our invention is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene.

The process of our invention is carried out at a temperature in the range of from about 10° C. up to about 150° C. with a temperature range of 50°–120° C. being preferred. The reaction time is inversely proportional to the reaction temperature, with lower reaction temperatures giving rise to greater reaction times; and, accordingly, the reaction time ranges from about 30 minutes up to about 10 hours.

In the reaction of our invention the mole ratio of 1-acetyl-3,3-dimethylcyclohexane to methallyl halide reactant is in the range of from 0.5:1.5 up to about 1.5:0.5 with a preferred ratio being from about 1:1 up to about 1:1.2.

The mole ratio of methallyl halide reactant in the reaction mass may be in the range of from about 0.75:1 up to about 1.5:1 with a preferred ratio of base:methallylic halide being from about 1:1 up to about 1.2:1.

The quantity of "phase transfer agent" in the reaction mass, based on the amount of 1-acetyl-3,3-dimethylcyclohexane in the reaction mass, may vary from 0.5 grams per mole of 1-acetyl-3,3-dimethylcyclohexane up to 25 grams per mole, with a preferred concentration of "phase transfer agent" beingin the range of from about 2.5 up to about 7.5 grams of "phase transfer agent" per mole of 1-acetyl-3,3-dimethylcyclohexane.

The reaction of our invention is preferably carried out at atmospheric pressure since that is the most convenient condition, however, lower or higher pressures can be used without detrimentally affecting the ultimate yield of desired reaction product.

The particular base used in the reaction is critical and preferred are sodium hydroxide and potassium hydroxide.

When the compounds having the generic structure:

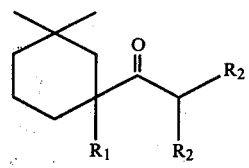

wherein $R_1$ or one or both of $R_2$ and/or $R_3$ is methallyl and the other of $R_1$ or $R_2$ and/or $R_3$ is hydrogen, (hereinafter referred to as "the 1-acetyl-3,3-dimethylcyclohexane derivatives of our invention") are used as food flavor adjuvants, the nature of the co-ingredients included with the 1-acetyl-3,3-dimethylcyclohexane derivatives of our invention in formulating the product composition will also serve to alter, modify, augment or enhance the organoleptic characteristics of the ultimate foodstuff treated therewith.

As used herein in regard to flavors, the terms "alter","modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the 1-acetyl-3,3-dimethylcyclohexane derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may be general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectines, and emulsifiers, e.g., mono- and diglycerides of fatty acids, skim milk power, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascene, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, cis-ethylidene-cis-3-hexenal, cis-ethylidene-trans-3-hexenal, cis-ethylidene-trans-3-heptanal, cis-ethylidene-trans-3-heptenal-diethylacetal, cis-3-ethylidene-4-octenal, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethyl-pyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxy-ethane, 1,1-dimethoxy-ethane and dimethoxy-methane).

The specific flavoring adjuvant selected for use may be either solid or liquid depending upon the desired physical form of the ultimate product, i.e., foodstuff, whether simulated or natural, and should, in any event, (i) be organoleptically compatible with the 1-acetyl-3,3-dimethylcyclohexane derivatives of our invention by not covering or spoiling the organoleptic properties (aroma and/or taste) thereof; (ii) be non-reactive with the 1-acetyl-3,3-dimethylcyclohexane derivatives of our invention; and (iii) be capable of providing an environment in which the 1-acetyl-3,3-dimethylcyclohexane derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 1-acetyl-3,3-dimethylcyclohexane derivatives of our invention employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the 1-acetyl-3,3-dimethylcyclohexane derivatives of our invention will, of course, substantially vitiate any possibility of obtaining the desired results while excess quantities provide needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the 1-acetyl-3,3-dimethylcyclohexane derivatives of our invention ranging from a small but effective amount, e.g., 0.5 parts per million up to about 100 parts per million based on total composition, are suitable. Concentrations in excess of the maximum quantity stated are not normally recommended since the fail to prove commensurate enhancement of organoleptic properties. In those instances, wherein one or more of the 1-acetyl-3,3-dimethylcyclohexane derivative(s) of our invention is(are) added to the foodstuff(s) as a (an) integral component(s) of flavoring composition(s), it is, of course, essential that the total quantity of flavoring composition employed by sufficient to yield an effective 1-acetyl-3,3-dimethylcyclohexane derivative concentration in the foodstuff product.

Food flavoring compositions prepared in accordance with the present invention preferably contain the 1-acetyl-3,3-dimethylcyclohexane derivative of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 1-acetyl-3,3-dimethylcyclohexane derivatives of our invention with, for example, gum arabic, gum tragacanth, carrageenan and the like, and the thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the 1-acetyl-3,3-dimethylcyclohexane derivatives of our invention in a dry blender until the requisite degree of uniformity is achieved.

It is presently preferred to combine with the 1-acetyl-3,3-dimethylcyclohexane derivatives of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Cis-ethylidene-cis-3-hexenal;
Cis-ethylidene-trans-3-hexenal;
Cis-ethylidene-trans-3-heptenal;
Cis-ethylidene-trans-3-heptenal-diethylacetal;
Cis-3-ethylidene-4-octenal;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
Damascone (1-crotonyl-2,2,6-trimethylcyclohex-1-one)
Damascenone (1-crotonyl-2,2,6-trimethylcyclohexa-1,5-diene)
Beta-cyclohomocitral (2,2,6-trimethylcyclohex-1-ene carboxaldehyde)
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-Hydroxy-4-methylpentyl) norbornadiene prepared according to U.S. application for Letters Patent No. 461,703, filed on Apr. 17, 1974

The 1-acetyl-3,3-dimethylcyclohexane derivatives of our invention and one or more auxiliary perfume ingredients, including, for example, alcohols, aldehydes, ketones, terpinic hydrocarbons, nitriles, esters, lactones, natural essential oils and synthetic essential oils, may be admixed so that the combined odors of the individual components produce a pleasant and desired fragrance, particularly and preferably in petitgrain fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute their particular olfactory characteristics, however, the over-all sensory effect of the perfume composition will be at least the sum total of the effects of each of the ingredients. Thus, the 1-acetyl-3,3-dimethylcyclohexane derivatives of our invention can be used to alter, modify or enhance the aroma characteristics of a perfume composition, for example, by utilizing or moderating the olfactory reaction contributed by another ingredient in the composition.

The amount of 1-acetyl-3,3-dimethylcyclohexane derivatives of our invention which will be effective in perfume compositions as well as in perfumed articles and colognes depends on many factors, including the other ingredients, their amounts and the effects which are desired. It has been found that perfume compositions containing as little as 0.01% of 1-acetyl-3,3-dimethylcyclohexane derivatives of our invention or even less (e.g., 0.005%) can be used to impart green, fruity, aldehydic notes with galbanum, ginger and citrus-like nuances to soaps, cosmetics or other products. The amount employed can range up to 70% of the fragrance components and will depend on considerations of cost, nature of the end product, the effect desired on the finished product and the particular fragrance sought.

The 1-acetyl-3,3-dimethylcyclohexane derivatives of our invention are useful [taken alone or together with other ingredients in perfume compositions] as (an) olfactory component(s) in detergents and soaps, space odorants and deodorants; perfumes; colognes; toilet water; bath preparations such as bubble bath and bath salts; hair preparations such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of 1-acetyl-3,3-dimethylcyclohexane derivatives of our invention will suffice to impart ginger, citrus and galbanum nuances to petitgrain aromas. Generally, no more than 3% of 1-acetyl-3,3-dimethylcyclohexane derivatives of our invention, based on the ultimate end product, is required in the perfume composition.

In addition, the perfume composition or fragrance composition of our invention can contain a vehicle, or carrier for the 1-acetyl-3,3-dimethylcyclohexane derivatives of our invention. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

Furthermore, 1-acetyl-3,3-dimethylcyclohexane derivatives of our invention are capable of supplying and/or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired green, sweet, fruity, floral and Virginia tobacco-like nuances prior to smoking and in the main and sidestreams on smoking, are created or enhanced and may be readily controlled and maintained at the desired uniform level regardless of variations in the tobacco components of the blend.

This invention further provides improved tobacco additives and methods whereby green, sweet, fruity, floral and Virginia tobacco-like nuances prior to smoking and in the main and sidestreams on smoking may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient 1-acetyl-3,3-dimethylcyclohexane derivatives of our invention.

In addition to the 1-acetyl-3,3-dimethylcyclohexane derivatives of our invention other flavoring and aroma additives may be added to the smoking tobacco materials or substitute therefor either separately or in mixture with the 1-acetyl-3,3-dimethylcyclohexane derivatives of our invention as follows:

I. Synthetic Materials:
  Beta-ethyl-cinnamaldehyde;
  Eugenol;
  Dipentene;
  Damascenone;
  Maltol;
  Ethyl Maltol;
  Delta undecalactone;
  Delta decalactone;
  Benzaldehyde;
  Amyl acetate;
  Ethyl butyrate;
  Ethyl valerate;
  Ethyl acetate;
  Beta-cyclohomocitral;
  2-Hexenol-1,2-methyl-5-isopropyl-1,3-nonadiene-8-one;
  2,6-Dimethyl-2,6-undecadiene-10-one;
  2-Methyl-5-isopropyl acetophenone;
  2-Hydroxy-2,5,5,8a-tetramethyl-1-(2-hydroxyethyl)-decahydronaphthalene;
  Dodecahydro-3a,6,6,9a-tetramethyl naphtho-(2,1-b)-furan;
  4-Hydroxy hexanoic acid, gamma lactone;
  Polyisoprenoid hydrocarbons defined in Example V of U.S. Patent 3,589,372 issued on June 29, 1971.

II. Natural Oils
  Celery seed oil;
  Coffee extract;
  Bergamot Oil;
  Cocoa extract;
  Nutmeg oil;
  Orignanum oil An aroma and flavoring concentrate containing 1-acetyl-3,3-dimethylcyclohexane derivatives of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of 1-acetyl-3,3-dimethylcyclohexane derivatives of our invention to smoking tobacco material is between 250 ppm and 1,500 ppm (0.025%–0.15%) of the active ingredients to the smoking tobacco material. We have further found that satisfactory results are obtained if the proportion by weight of the sum total of 1-acetyl-3,3-dimethylcyclohexane derivatives of our invention used to flavoring material is between 2,500 and 10,000 ppm (0.25%–1.5%).

Any convenient method for incorporating the 1-acetyl-3,3-dimethylcyclohexane derivatives of our invention in the tobacco product may be employed. Thus, the 1-acetyl-3,3-dimethylcyclohexane derivatives of our invention taken alone or along with other flavoring additives may be dissolved in a suitable solvent such as ethanol, pentane, diethyl ether and/or other volatile organic solvents and the resulting solution may either be spread on the cured, cased and blended tobacco material or the tobacco material may be dipped into such solution. Under certain circumstances, a solution of the 1-acetyl-3,3-dimethylcyclohexane derivatives of our invention taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefore need be treated and the thus treated tobacco may be blended with other tobaccos before the ultimate tobacco product is formed. In such cases, the tobacco treated may have the 1-acetyl-3,3-dimethylcyclohexane derivatives of our invention in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 1-acetyl-3,3-dimethylcyclohexane derivatives of our invention in an amount to provide a tobacco composition containing 800 ppm by weight of 1-acetyl-3,3-dimethylcyclohexane derivatives of our invention on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and sidestreams when the cigarette is smoked. This aroma is described as having green, sweet, fruity, floral and Virginia tobacco-like nuances prior to smoking and in the main and sidestreams on smoking.

While our invention is particularly useful in the manufacture of smoking tobacco, such as cigarette tobacco, cigar tobacco and pipe tobacco, other tobacco products formed from sheeted tobacco dust or fines may also be used. Likewise, the 1-acetyl-3,3-dimethylcyclohexane derivatives of our invention can be incorporated with materials such as filter tip materials, seam paste, packaging materials and the like which are used along with tobacco to form a product adapted for smoking. Furthermore, the 1-acetyl-3,3-dimethylcyclohexane derivatives of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or both substitute materials or both.

It will thus be apparent that the 1-acetyl-3,3-dimethylcyclohexane derivatives of our invention can be utilized to alter, modify or enhance sensory properties, such as flavor(s) and/or fragrance(s) of a wide variety of consumable materials.

The following examples serve to illustrate our invention and the invention is to be considered restricted thereto only as indicated in the appended claims.

All parts and percentages given herein are by weight unless otherwise specified.

EXAMPLE I

PREPARATION OF 1-ACETYL-1-METHALLYL-3,3-DIMETHYLCYCLOHEXANE AND 1-(2-METHALLYL-5-METHYL-4-PENTENOYL)-3,3-DIMETHYLCYCLOHEXANE

Reaction:

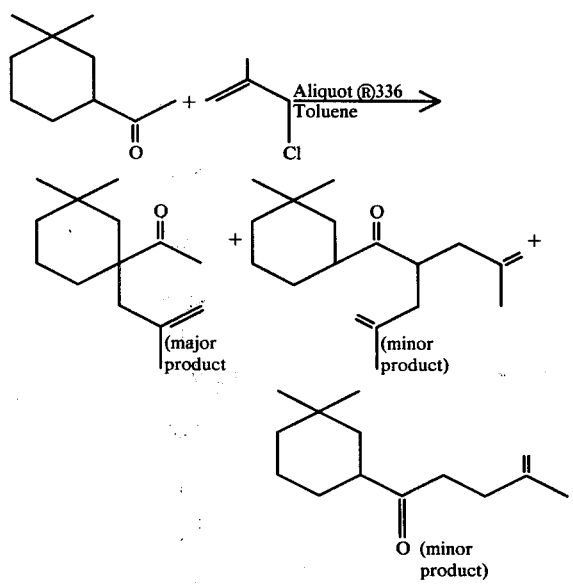

A slurry of 1-acetyl-3,3-dimethylcyclohexane (624 grams, 4 moles), granular sodium hydroxide (240 grams, 6 moles), Aliquot ® 336 (tricaprylmethylammonium chloride [35 grams]), methallyl chloride (432 grams, 4.8 moles), and 400 ml of toluene is heated at reflux for 4 ¼ hours. At the end of this time, one liter of water is added to the cooled reaction mass. The aqueous layer is discarded, and the organic layer is distilled rapidly through a short column to afford 203 grams of recovered 1-acetyl-3,3,-dimethylcyclohexane, 500 grams of 1-acetyl-3,3-dimethyl-1-methallyl cyclohexane, and 73 grams of 3,3-dimethyl-1-(2-methyllyl-5-methyl-4-pentenoyl)cyclohexane) (1°–4°, 3.0 mm Hg) containing 5% of 3,3-dimethyl-1-(4-methyl-4-pentenoyl). A portion of the latter compound is isolated by GLC chromatography (1'×⅛" 80% SE-30 packed column; 200° C. isothermal) and exhibits the following odor and flavor properties:

ODOR PROPERTIES

Green;
Herbaceous;
Melony;
Fruity;
Galbanum-like;
Ginger-like; and
Citrusy.

FLAVOR PROPERTIES:

Fatty;
Sweet;
Fruity;
Citrus;
Green;
Vegetable-like; and
Waxy.

The NMR analysis for the compounds set forth below is as follows:

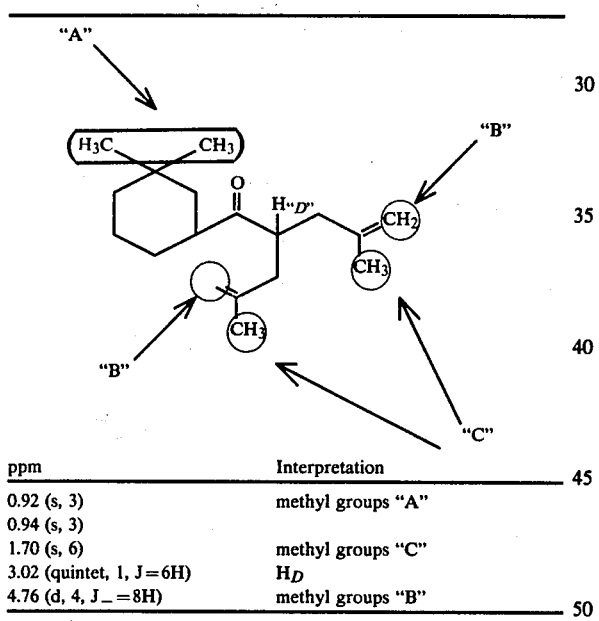

| ppm | Interpretation |
|---|---|
| 0.92 (s, 3) | methyl groups "A" |
| 0.94 (s, 3) | |
| 1.70 (s, 6) | methyl groups "C" |
| 3.02 (quintet, 1, J=6H) | $H_D$ |
| 4.76 (d, 4, J_=8H) | methyl groups "B" |

The Infrared analysis is as follows:
C=O 1695 cm$^{-1}$
C=CH$_2$ 1635 cm$^{-1}$

The Mass Spectral analysis is as follows:
MW-262 (confirmed by GC-MS)

Figure 2:
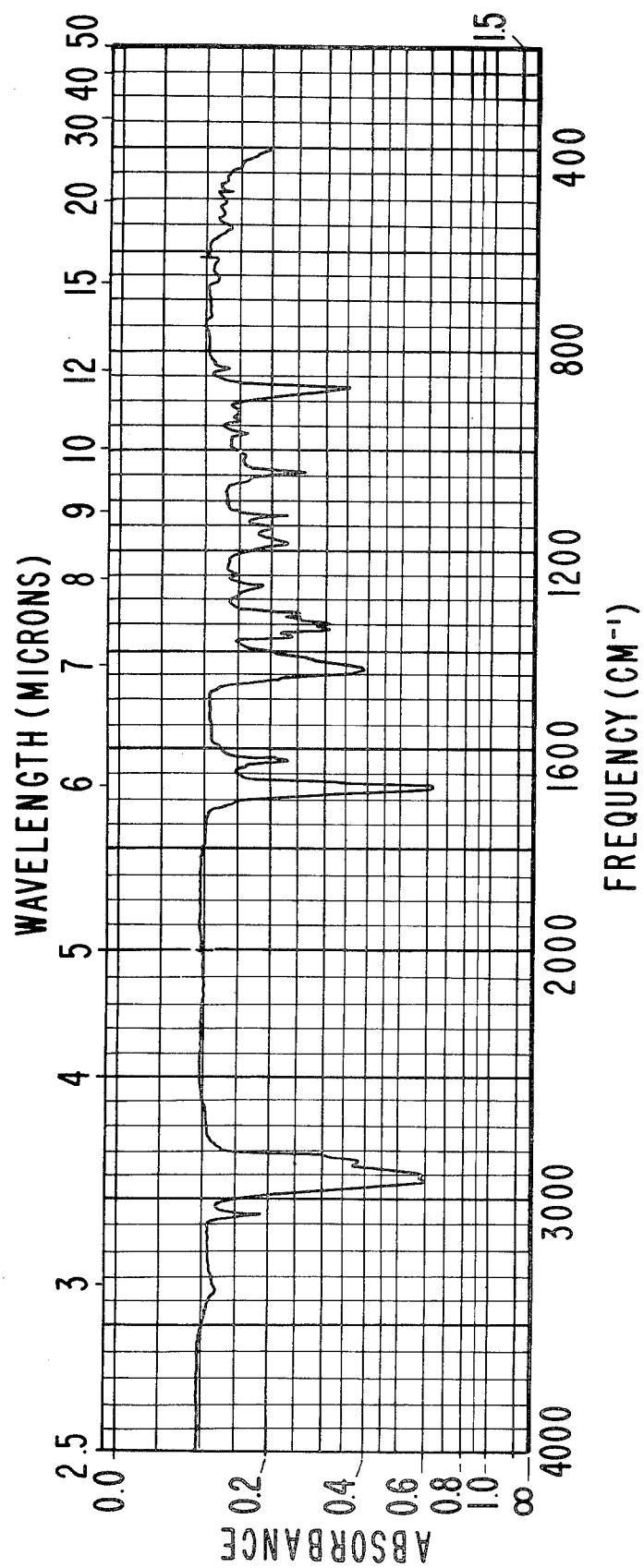
FIG. 2 represents the Infrared spectrum for 1-acetyl-1-methallyl-3,3-dimethylcyclohexane produced according to Example I.

The NMR spectrum is set forth in FIG. 1 for 1-acetyl-3,3-dimethyl-1-methallylcyclohexane. The Infrared spectrum is set forth in FIG. 2 for 1-acetyl-3,3-dimethyl-1-methyallylcylcohexane.

The NMR spectrum for 3,3-dimethyl-1-(2-methallyl-5-methyl-4-pentenoyl) cyclohexane is set forth in FIG. 3. The Infrared spectrum is set forth in FIG. 4.

EXAMPLE II

Reaction:

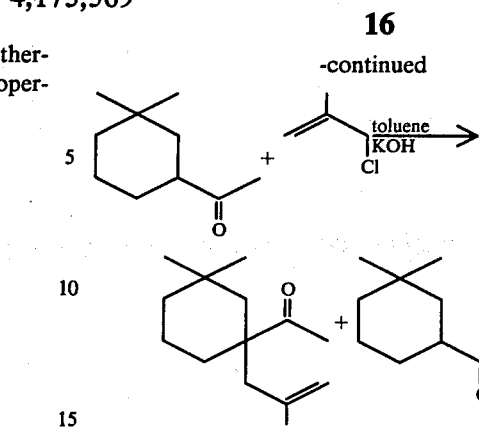

A slurry of 1-acetyl-3,3-dimethylcyclohexane (156 grams, 1 mole), potassium hydroxide (86 grams, 1.5 moles), and toluene (300 ml) is heated to reflux. Methallyl chloride (135 grams, 1.5 moles) is added to the thickened reaction mass whereupon the mass becomes more fluid. The mixture is heated at reflux for 6 ½ hours. At the end of this period, the reaction mass is cooled to room temperature, and 500 ml of water are added thereto. The aqueous layer is discarded, and the organic layer is distilled to afford recovered 1-acetyl-3,3-dimethylcyclohexane (86 gm), 1-acetyl-3,3-dimethyl-1-methallylcyclohexane (67 gm, containing 2% 3,3-dimethyl-1-(4-methyl-4-pentenoyl) cyclohexane) (NMR Spectrum FIG. 1; IR spectrum, FIG. 2), and 3,3-dimethyl-1-(4-methyl-4-pentenoyl)cyclohexane (12 gm).

EXAMPLE III

Reaction:

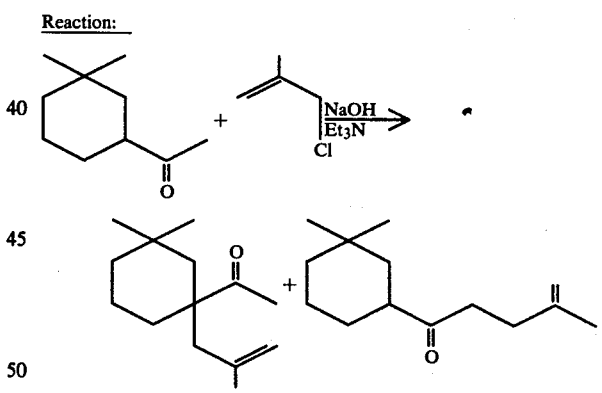

A mixture of 1-acetyl-3,3-dimethylcyclohexane (156 grams, 1 mole) sodium hydroxide (60 grams, 1.5 moles), methallyl chloride (135 grams, 1.5 moles) and triethylamine (10 grams) is stirred and heated at 80°-84° C. for 12 hours. The reaction mass is cooled to room temperature. Water is added with stirring, and the aqueous layer is discarded. The organoc layer is distilled to afford 1-acetyl-3,3-dimethylcyclohexane (62.4 gm), 1-acetyl-3,3-dimethyl-1-(2-methyl-2-propenyl)cyclohexane (80 gm), (NMR spectrum, FIG. 1; IR spectrum, FIG. 2), and 3,3-dimethyl-1-(4-methyl-4-pentenoyl)cyclohexane (8 gm).

EXAMPLE IV

Reaction:

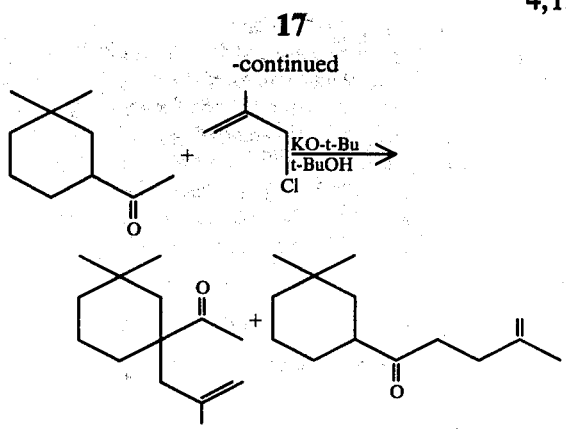

A fresh solution of potassium-t-butoxide is prepared by adding potassium metal (28 grams, 0.72 moles) to 500 ml of anhydrous t-butanol under a nitrogen blanket. 1-Acetyl-3,3-dimethylcyclohexane is added thereto, and the resulting mixture is stirred at room temperature for 1 hour. Methallyl chloride (74.4 grams, 0.8 moles) is added, and the reaction mass is allowed to stir for an additional hour. The mixture is filtered to remove potassium chloride, and the t-butanol is removed by evaporation on a rotary evaporator. The residual oil is distilled to afford a mixture of 1-acetyl-3,3-dimethylcyclohexane, 1-acetyl-3,3-dimethyl-1-(2-methyl-2-propenyl) cyclohexane, (NMR spectrum, FIG. 1; IR spectrum, FIG. 2) and 3,3-dimethyl-1-(4-methyl-4-pentenoyl) cyclohexane.

EXAMPLE V

PREPARATION OF 1-ACETYL-3,3-DIMETHYL-(2-METHYL-2-PROPENYL) CYCLOHEXANE

Reaction:

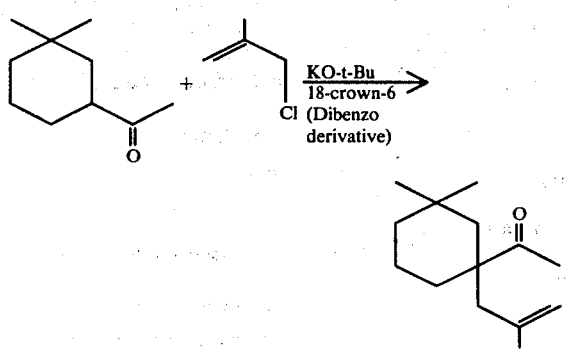

A slurry of potassium hydroxide (84 grams, 1.5 moles), 1-acetyl-3,3,-dimethylcyclohexane (156 grams, 1 mole), dibenzo-18-crown-6 (3 grams) having the structure:

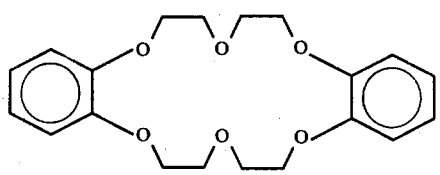

produced by the Aldrich Chemical Company of Metuchen, New Jersey, and toluene (150 ml) is heated to reflux whereupon the reaction mass thickens. The mass is cooled to 70° C., and methallyl chloride (135 grams, 1.5 moles) is added thereto rendering the reaction mixture more fluid. The reaction mixture is heated at reflux for an additional 9 hours whereupon the mass is cooled, and water is added. The aqueous layer is decanted and the organic layer is distilled to afford 1-acetyl-3,3-dimethylcyclohexane (62 gm) and 1-acetyl-3,3-dimethyl-1-(2-methyl-2-propenyl) cyclohexane (83 gm, NMR spectrum, FIG. 1; IR spectrum, FIG. 2).

EXAMPLE VI

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes.

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the mixture of 1-acetyl-1-methallyl-3,3-dimethylcyclohexane and 1-(2-methallyl-5-methyl-4-pentenoyl)-3,3-dimethylcyclohexane produce according to Example I at 100 ppm per cigarette. Another third of these model cigarettes are treated in the filter with the mixture of 1-acetyl-1-methallyl-3,3-dimethylcyclohexane and 1-(2-methallyl-5-methyl-4-pentenoyl)-3,3-dimethylcyclohexane at the rate of $2\times10^{-5}$ gm. and $3\times10^{-5}$ gm. When evaluated by paired comparison, the cigarettes treated both in the tobacco and in the filter with the mixture of 1-acetyl-1-methallyl-3,3-dimethylcyclohexane and 1-(2-methallyl-5-methyl-4-pentenoyl)-3,3-dimethylcyclohexane are found, in smoke flavor, to have a green, sweet, fruity, floral and Virginia tobacco-like flavor and aroma nuance in the mainstream and in the sidestream on smoking and, in addition, prior to smoking.

EXAMPLE VII

A tobacco blend in made up by mixing the following materials.

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |

-continued

| Ingredient | Parts by Weight |
| --- | --- |
| Glycerine | 2.8 |
| Water | 5.3 |

The above tobacco is used in producing cigarettes and the following formulation is compounded and incorporated into each of these cigarettes.

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 1-acetyl-1-methallyl-3,3-dimethylcyclohexane produced according to Example V at 100 ppm per cigarette. Another third of these model cigarettes are treated in the filter with 1-acetyl-1-methallyl-3,3-dimethylcyclohexane at the rate of $2 \times 10^{-5}$ gm. and $3 \times 10^{-5}$ gm. When evaluated by paired comparison, the cigarettes treated both in the tobacco and in the filter with 1-acetyl-1-methallyl-3,3-dimethylcyclohexane are found, in smoke flavor, to have a green, sweet, fruity, floral and Virginia tobacco-like flavor and aroma nuance in the mainstream and in the sidestream on smoking and, in addition, prior to smoking.

EXAMPLE VIII

A tobacco blend is made up by mixing the following materials:

| Ingredient | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes.

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the 1-acetyl-1-methallyl-3,3-dimethylcyclohexane produced according to one of Examples II, III or IV at 100 ppm per cigarette. Another third of these model cigarettes are treated in the filter with the 1-acetyl-1-methallyl-3,3-dimethylcyclohexane at the rate of $2 \times 10^{-5}$ gm. and $3 \times 10^{-5}$ gm. When evaluated by paired comparison, the cigarettes treated both in the tobacco and in the filter with the 1-acetyl-1-methallyl-3,3-dimethylcyclohexane are found, in smoke flavor, to have a green, sweet, fruity, floral and Virginia tobacco-like flavor and aroma nuance in the mainstream and in the sidestream on smoking and, in addition, prior to smoking.

EXAMPLE IX

ORANGE FLAVOR FORMULATION

An orange flavor formulation is prepared by admixing:

| Ingredient | Parts |
| --- | --- |
| Natural orange oil | 13.00 |
| Acetaldehyde | 1.50 |
| Ethyl acetate | 0.10 |
| Ethyl butyrate | 0.50 |
| Propanal | 0.10 |
| trans-2-Hexenal | 0.10 |
| Ethyl alcohol (95%) | 60.00 |
| Fusel Oil | 0.05 |
| Propylene Glycol | 24.65 |

This is denominated Flavor "A". A second formulation, Flavor "B" is prepared by adding 1-acetyl-1-methallyl-3,3-dimethylcyclohexane (one percent in ethanol) to a portion of Flavor "A" in the ratio of 2 parts to 100 parts of Flavor "A".

Each of Flavors "A" and "B" is added in the amount of two ounces per gallon of 32° Baume sugar syrup to produce a syrup for combination with water to form a drink. The beverage prepared using Flavor "A" is a passable orange beverage of good character, flavor and intensity.

The beverage prepared using Flavor "B" has a much improved flavor. The improvement contributed by the 1-acetyl-1-methallyl-3,3-dimethylcyclohexane is due to:
1. a greater degree of the natural character of freshly squeezed orange juice
2. greater orange juice flavor depth.

EXAMPLE X

PERFUME FORMULATION

A perfume formulation is prepared by admixing:

| Ingredients | Parts |
| --- | --- |
| Linalool | 30 |
| Linalyl acetate | 10 |
| Terpineol coeur | 5 |
| Nerol coeur | 10 |
| Terpinyl acetate | 2 |
| Geranyl acetate | 2 |
| Neryl acetate | 2 |
| Methyl anthranilate | 1 |
| Citral | 10 |
| n-Decyl alcohol | 1 |
| n-Dodecyl alcohol | 5 |
| n-Dodecanal | 15 |
| n-Decanal | 30 |
| n-Nonanol | 3 |
| n-Nonanal | 5 |
| n-Decyl acetate | 5 |
| n-Dodecyl acetate | 3 |
| 1-acetyl-1-methallyl-3,3-dimethyl cyclohexane (Produced by Example I) | 5 |

The 1-acetyl-1-methallyl-3,3-dimethylcyclohexane imparts a natural, tart, orange character to this terpeneless orange perfume formulation.

What is claimed is:

1. A smoking tobacco composition comprising in intimate admixture (i) smoking tobacco and (ii) a tobacco flavor composition comprising the compound having the structure:

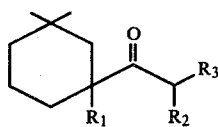

wherein $R_1$ is methyllyl, $R_2$ is hydrogen and $R_3$ is hydrogen, or wherein $R_1$ is hydrogen, $R_2$ is methyllyl and $R_3$ is methyllyl.

2. A smoking article comprising (i) tobacco or a tobacco substitute and (ii) a flavorant for said tobacco or tobacco substitute comprising the compound having the structure:

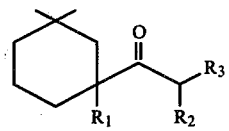

wherein $R_1$ is methyllyl, $R_2$ is hydrogen and $R_3$ is hydrogen, or wherein $R_1$ is hydrogen, $R_2$ is methyllyl and $R_3$ is methyllyl.

3. A process for augmenting or enhancing the aroma or taste of a smoking tobacco comprising the step of adding to smoking tobacco an aroma or taste-augmenting or enhancing quantity of the compound having the structure:

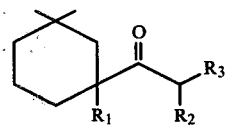

wherein $R_1$ is methyllyl, $R_2$ is hydrogen and $R_3$ is hydrogen, or wherein $R_1$ is hydrogen, $R_2$ is methyllyl and $R_3$ is methyllyl.

* * * * *